United States Patent [19]

Isaacs et al.

[11] Patent Number: 4,997,851

[45] Date of Patent: Mar. 5, 1991

[54] ANTIVIRAL AND ANTIBACTERIAL ACTIVITY OF FATTY ACIDS AND MONOGLYCERIDES

[76] Inventors: Charles E. Isaacs, Manalapan, N.J.; Halldor Thomar, Reyjavik, Iceland; Kwang S. Kim, Staten Island; William C. Heird, New York, both of N.Y.

[21] Appl. No.: 140,078

[22] Filed: Dec. 31, 1987

[51] Int. Cl.[5] .................. A61K 31/20; A61K 31/22; A61K 31/23

[52] U.S. Cl. ..................... 514/558; 514/546; 514/549; 514/552; 514/560

[58] Field of Search ............... 514/546, 547, 549, 552, 514/557, 558, 560

[56] References Cited

U.S. PATENT DOCUMENTS

| 4,489,097 | 12/1984 | Stone | 514/557 |
| 4,513,008 | 4/1985 | Revici et al. | 514/703 |
| 4,806,352 | 2/1989 | Cantrell | 514/937 |

*Primary Examiner*—Douglas W. Robinson
*Assistant Examiner*—Zohreh A. Fay
*Attorney, Agent, or Firm*—Kane, Dalsimer, Sullivan, Kurucz, Levy, Eisele and Richard

[57] ABSTRACT

This invention is directed to antiviral and antibacterial activity of fatty acids and monoglycerides. More particularly, this invention is directed to the inactivation of enveloped viruses and the killing of cells by fatty acids and monoglycerides. The invention is also directed to an antiviral and/or antibacterial pharmaceutical composition consisting essentially of inert pharmaceutical carrier and an effective amount of one or more compounds selected from the group consisting of fatty acids and monoglycerides thereof.

9 Claims, 2 Drawing Sheets

ANTIVIRAL AND ANTIBACTERIAL ACTIVITY OF FATTY ACIDS AND MONOGLYCERIDES

FIELD OF THE INVENTION

This application is directed to antiviral and antibacterial activity of fatty acids and monoglycerides. More particularly, this application is directed to the inactivation of enveloped viruses and the killing of cells by fatty acids and monoglycerides.

BACKGROUND OF THE INVENTION

There are many published reports concerning the ability of human milk to protect the suckling infant from gastrointestinal infection. See, A. S. Cunningham, Morbidity in breast-fed and artificially fed infants, *J. Pediatr.*, 1979, Vol. 95, p. 685-689; M. G. Myers et al., Respiratory and gastrointestinal illnesses in breast- and formula-fed infants, *Am. J. Dis. Child.*, 1984, Vol. 138, p. 629-632; S. A. Larsen, Jr., Relation of breast versus bottle feeding to hospitalization for gastroenteritis in a middle-class U.S. population, *J. Pediatr.*, 1978, Vol. 92, p. 417-418; M. E. Fallot et al., Breast-feeding reduces incidence of hospital admissions for infection in infants, *Pediatr.*, 1980, Vol. 65, p. 1121-1124; A. S. Cunningham, Breast-feeding and health, *J. Pediatr.*, 1987, Vol. 110, p. 658-659. Much of this protection has been attributed to the presence of immunogobulins in the milk. See, G. A. Loslonsky et al., Maternal-neonatal interactions and human breast milk, *In: Reproductive Immunology*, N. Gleicher (ed.), New York, Alan R. Riss, 1981, p. 171-182; A. S. Goldman et al., Host defenses: development and maternal contributions, *In: Barness LA.*, ed., *Advance in pediatrics*, Vol. 32, 1985, p. 71-100. However, it has also been shown that there are nonspecific factors in milk which can kill pathogens or slow their replication. Some of these protective factors are also nutrients, such as monoglycerides and fatty acids. Since human infant formula does not contain immunoglobulins, it has been assumed that it does not confer any protection against gastrointestinal infection. However, formulas do contain triglycerides which, following lipolysis in the stomach and intestine, produce free fatty acids and monoglycerides of which some have been shown to inactivate enveloped viruses and *Giardia lamblia* when present in human and bovine milk. See, J. K. Welsh et al., Use of Semliki Forest virus to identify lipid-mediated antiviral activity and anti-alphavirus immunoglobulin A in human milk, *Infect. Immun.*, 1978, Vol. 19, p. 395-401 (I); J. K. Welsh et al., Effect of antiviral lipids, heat, and freezing on the activity of viruses in human milk, *J. Infect. Dis.*, 1979, Vol. 140, p. 322-328 (II); C. E. Isaacs et al., Membrane disruptive effect of human milk: Inactivation of enveloped viruses, *J. Infect. Dis.*, 1986, Vol. 154, p. 966-971, all of the aforementioned articles being incorporated herein by reference.

Human milk contains a number of antiviral factors that are not immunoglobulins. See, W. A. Falkler, Jr., et al., A lipid inhibitor of dengue virus in human colostrum and milk, *Arch. Virol.*, 1975, Vol. 47, p. 3-10; A. H. Fieldsteel, Non-specific antiviral substances in human milk active against arbovirus and murine leukemia virus, *Cancer Res.*, 1974, Vol. 34, p. 712-715; T. H. Matthews et al., Antiviral activity in milk of possible clinical importance, *Lancet*, 1976, Vol. ii, p. 1387-1389; N. H. Sarkar et al., Effect of human milk on the mouse mammary tumor virus, *Cancer Res.*, 1973, Vol. 33, p. 626-629. Some of these factors are located in the non-lipid fraction of the milk, but most studies found antiviral activity associated with the lipid fraction. Antiviral lipids were best characterized by Welsh et al. (II), who found that free unsaturated fatty acids and monoglycerides in milk inactivated enveloped, but not nonenveloped, viruses.

As reported in C. E. Isaacs et al., Membrane Disruptive Effect of Human Milk: Inactivation of Enveloped Viruses, *J. Infect. Dis.*, 1986, Vol. 154, p. 966-971, specifically incorporated herein by reference, the work of Welch et al. (II) has been confirmed and extended. It was shown that lipids from fresh breast milk are not antiviral but become active against enveloped viruses upon storage at 4° C. and in infant stomachs, probably by the release of fatty acids from milk triglycerides.

DESCRIPTION OF THE INVENTION

Figure 1A:
FIGS. 1a to 1c represent negative staining of VSV particles showing the effect of linoleic acid. VSV was incubated at 37° C. for 30 min in (a) MM, (b) linoleic acid (0.5 mg/ml of MM), and (c) linoleic acid (1 mg/ml of MM). (a) Normal intact particles covered with spikes, (b) Viral envelope no longer intact, allowing penetration of stain into most particles, (c) Virus particles in various stages of disintegration. Bar=0.1 μm.

Lipids in fresh human milk do not inactivate viruses but become antiviral after storage of the milk for a few days at 4 or 23° C. The appearance of antiviral activity depends on active milk lipases and correlates with the release of free fatty acids in the milk. A number of fatty acids which are normal components of milk lipids were tested against enveloped viruses, i.e., vesicular stomatitis virus, herpes simplex virus, and visna virus, and against a nonenveloped virus, poliovirus. Short-chain and long-chain saturated fatty acids had no or a very small antiviral effect at the highest concentrations tested. Medium-chain saturated and long-chain unsaturated fatty acids, on the other hand, were all highly active against the enveloped viruses, although the fatty acid concentration required for maximum viral inactivation varied by as much as 20-fold. Monoglycerides of these fatty acids were also highly antiviral, in some instances at a concentration 10 times lower than that of the free fatty acids. None of the fatty acids inactivated poliovirus. Antiviral fatty acids were found to affect the viral envelope, causing leakage and at higher concentrations, a complete disintegration of the envelope and the viral particles. They also caused disintegration of the plasma membranes of tissue culture cells resulting in cell lysis and death. The same phenomenon occurred in cell cultures incubated with stored antiviral human milk. The antimicrobial effect of human milk lipids in vitro is therefore most likely caused by disintegration of cellular and viral membranes by fatty acids.

MATERIALS AND METHODS

Cell cultures. Vero cells (African green monkey kidney cell line; Flow Laboratories Inc., McLean, Va.) were grown in Eagle basal medium (BME) (GIBCO Laboratories, Grand Island, N.Y.) with 10% inactivated fetal bovine serum (GIBCO). Sheep fibroblast cultures were obtained from the choroid plexus of a lamb brain and grown in 15% lamb serum (Colorado Serum Co.) in BME. The maintenance medium (MM) for Vero cells was BME with 2% fetal bovine serum; for sheep cells, the MM was 2% lamb serum in BME. Gentamicin (0.1%) was added to all media.

Viruses. Vesicular stomatitis virus (VSV) strain Indiana and herpes simplex virus type 1 (HSV-1) strain MacIntyre were obtained from the American Type Culture Collection, Rockville, Md., and grown in Vero cells. Visna virus strain K796 was grown in sheep choroid plexus cells. Poliovirus type 1 strain Chat was obtained from R. I. Carp (New York Institute for Basic Research) and grown in Vero cells.

Virus titration. Viruses were titrated by inoculation of 10-fold dilutions (VSV, poliovirus, and HSV-1 were inoculated into Vero cell cultures, and visna virus was inoculated into sheep choroid plexus cell cultures) in 96-well microtiter tissue culture plates (Becton Dickinson Labware, Oxnard, Calif.). A virus dilution (0.1 ml) in MM was inoculated into each well with four wells per dilution. The plates were kept for 2 to 12 days, depending on the virus, and examined daily for cytopathic effect. Virus titers were calculated by the method of Reed and Muench (L. J. Reed et al., *Am. J. Hyg.*, 1938, Vol. 27, p. 493–497).

Milk samples. Human milk samples 1, 2, and 3 were collected under sterile conditions 1 to 5 months postpartum and kept deep-frozen at $-86°$ C. until used in experiments.

Reagents Fatty acids and monoglycerides were purchased from Sigma Chemical Co., St. Louis, Mo. (purest grade). Immediately before use they were melted and emulsified in liquid form in BME with 10% fetal bovine serum by vortexing at the highest speed for 1 min. The emulsions (100 mg/ml) were diluted to the desired concentrations in MM. Emulsions of short-chain fatty acids were neutralized to pH 7 by addition of 1M NaOH. Unsaturated fatty acids and monoglycerides were kept under nitrogen, and emulsions were used within a few minutes of preparation. Eserine sulfate (physostigmine; Sigma) and NaCl were dissolved in water and diluted in MM before use in experiments.

Assay of antiviral activity. About $10^5$ 50% tissue culture infective doses (TCID$_{50}$s) of virus were mixed with a fivefold dilution of milk in MM or with an emulsion of fatty acids and monoglycerides in MM and incubated at 37° C. for 30 min. Virus mixed with MM alone was used as a control. After incubation, the infectivity of each mixture was titrated by the serial dilution endpoint method. Dilutions (10-fold) were made in MM. The $10^{-2}$ to $10^{-5}$ dilutions were inoculated into monolayers of Vero cells, and the virus titers were determined as described above. The difference between the titer ($\log_{10}$) of the control virus and the titers of milk-virus and lipid-virus mixtures, i.e., the reduction of virus titer, was used as a measure of antiviral activity.

Preparation of virus for electron microscopy. VSV was concentrated and partially purified by differential centrifugation in a Beckman L2-65B ultracentrifuge, and samples ($10^{10}$ TCID$_{50}$/ml) were incubated at 37° C. for 30 min. in MM with or without emulsified fatty acids. The virus suspensions were applied to carbon-coated grids and negatively stained with 2% phosphotungstic acid, pH 7.0. Specimens were examined by using a Hitachi HS 8-2 electron microscope at 50 kV.

Preparation of cells for electron microscopy. Monolayer cultures of cells were incubated for 30 min. at 37° C. either in MM alone or with milk or a fatty acid emulsion. The cell layers were then carefully rinsed with Hanks balanced salt solution and fixed with 2% glutaraldehyde in 0.1M cacodylate buffer. After rinsing in buffer and postfixation with 2% osmium tetroxice, the cells were dehydrated through gradings of ethanol, critical-point dried, and sputter coated with 10.5 nm of gold. They were examined in an ISI-ISS40 scanning electron microscope at 20 kV.

Estimation of free fatty acids levels. Lipids from 100 $\mu$l of the milk samples were extracted with 0.5 ml of chloroform-methanol (2:1). The upper phase was removed, and an aliquot of the chloroform layer was separated by thin-layer chromatography on Silica Gel G (Merck & Co., Inc., Rahway, N.J.) plates with quantitative standards of oleic acid in a solvent system consisting of hexane-diethyl etheracetic acid (70:30:1.5). The developed plates were charred after spraying with dichromate-sulfuric acid, and the free fatty acids were quantitated by densitometry.

RESULTS

Relationship between lipolysis and antiviral activity. Previous results (Isaacs et al.) showed that human milk becomes active against enveloped viruses after storage at 4°, 23°, or $-20°$ C. for various lengths of time. The antiviral activity is associated with the cream fraction, but the skim fraction is needed for the lipids to become antiviral. To test whether the appearance of antiviral activity depended on active milk lipases, milk samples 1, 2, and 3 were stored at 4° C. for 4 days with or without two lipase inhibitors, 5 mM eserine sulfate and 1M NaCl. The virus titer (VSV) fell from $10^5$ to $\leq 10^{1.5}$ TCID$_{50}$ after incubation with milk stored without an inhibitor, thus showing a reduction of $10^{3.5}$ TCID$_{50}$. In contrast, virus incubated in the same way with milk which had been stored with lipase inhibitors showed no loss of infectivity at the concentrations used. The inhibitors had no effect on milk which was already antiviral.

Another indication that the appearance of antiviral activity in stored human milk is associated with lipolysis is shown in Table 1. Deep-frozen human milk sample 1 did not have a detectable level of free fatty acids, but the level increased to 7 and 12 mg/ml upon storage at 4° and 23° C., respectively, for 4 days. Both stored samples were highly antiviral. The free fatty acid level of milk sample 3, on the other hand, increased to only 2 mg/ml upon storage, and the milk did not become antiviral. Compared with milk sample 3, milk sample 1 had much higher levels of lipoprotein lipase, which was previously shown to correlate with the appearance of milk antiviral activity.

Antiviral activity of fatty acids and monoglycerides. A comparison of the antiviral activity of a number of fatty acids found in milk is shown in Table 2. Short-chain (butyric, caproic, and caprylic) and long-chain saturated (palmitic and stearic) fatty acids had no or a very small antiviral effect at the highest concentrations tested. On the other hand, the medium-chain saturated and long-chain unsaturated fatty acids were all antiviral but at different concentrations. Table 2 shows the lowest concentration causing a >10,000-fold reduction in VSV titer. A 2-fold-lower concentration either did not inactivate the virus or caused only a 10-fold reduction in titer. Similar results were obtained for HSV-1 and visna virus, a retrovirus. In contrast, incubation of poliovirus at 37° C. for 30 min. with capric, lauric, myristic, palmitoleic, oleic, linoleic, linolenic, and arachidonic acids, each at a concentration of 8 mg/ml, did not cause a significant reduction of virus titer compared with the titer of poliovirus incubated without fatty acids ($10^{4.7}$ TCID$_{50}$). The sodium salts of oleic and linoleic acids had antiviral effects similar to those of the free acids.

Other products of lipolysis, e.g., 1-monoglycerides of fatty acids, were also tested for antiviral activity (Table 3). All the monoglycerides tested except monomyristin and monoolein were antiviral in concentrations 5 to 10 times lower (millimolar) than those of the corresponding fatty acids.

The above experiments with human milk, milk stomach contents, and purified lipids show that MGs and fatty acids which are released from human milk triglycerides either during storage or in the gastrointestinal tract kill enveloped viruses and very likely serve an in vivo protective role in breast-fed infants.

Studies have also been done to determine the time required for viral inactivation. Virus was incubated with monolaurin (12:0) in maintenance media:

TABLE 3A

Time Course of Viral Inactivation

| Incubation Time (min) | Reduction of HSV-1 titer |
|---|---|
| 30 | ≧4.0 |
| 10 | ≧4.0 |
| 5 | ≧4.0 |
| 1 | ≧4.0 |
| 0.5 | ≧4.0 |

These results indicate that viral killing is rapid and probably happens as the MG or FFA comes into contact with the viral envelope. Electron micrographs with negative staining of VSV incubated with linoleic acid showed that at 0.5 mg per ml leakage of viral envelopes was produced allowing the stain to enter many particles. The effect was far more pronounced with 1 mg of linoleic acid per ml, causing particle disintegration.

Figure 1B:
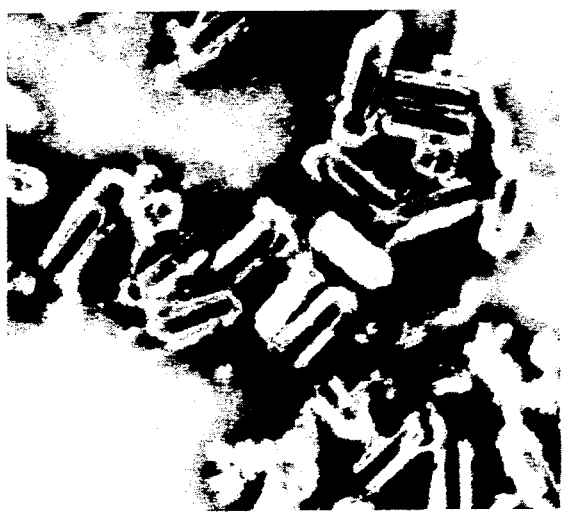

Effect of fatty acids on viral particles. To study the effect of fatty acids on virus particles, VSV was concentrated, partly purified, and then incubated at 37° C. for 30 min in MM with or without linoleic acid. Negative staining of virus incubated without fatty acids showed an abundance of characteristic bullet-shaped particles covered with spikes and containing coiled nucleocapsids (FIG. 1a). Incubation with 0.5 mg of linoleic acid per ml caused leakage of viral envelopes, allowing the stain to enter many particles (FIG. 1b). The effect was far more pronounced with 1 mg of linoleic acid per ml (FIG. 1c), causing particle disintegration. Titration of the samples used for electron microscopy showed a <10-fold reduction in virus titer with 0.5 mg of linoleic acid per ml, whereas 1 mg/ml caused a ≧1,000-fold reduction. Similar results were obtained by negative staining of VSV incubated with low concentrations of arachidonic acid.

Figure 2B:
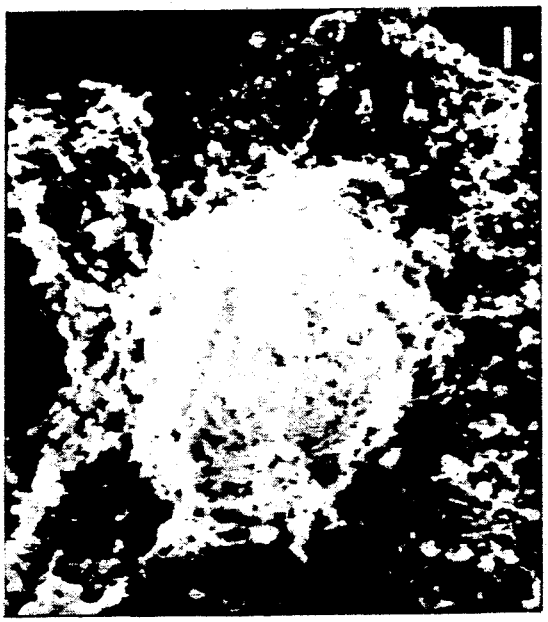
FIGS. 2a to 2d represent scanning electron micrographs of all cultures showing the effect of human milk and linoleic acid. Vero cells were incubated at 37° C. for 30 min in (a) human milk, (b) milk stored at 4° C. for 4 days, (c) MM, or (d) linoleic acid (1 mg/ml of MM). Milk samples were diluted 1:5 in MM. (a and c) Intact cell membranes with microvilli. (b and d) Cell membranes partly or completely disintegrated. Bar=1.0 μm.
Figure 2D:
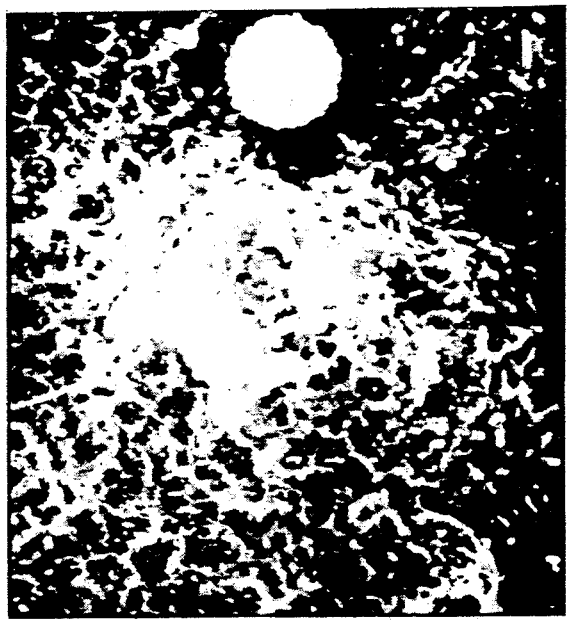
Figure 2A:
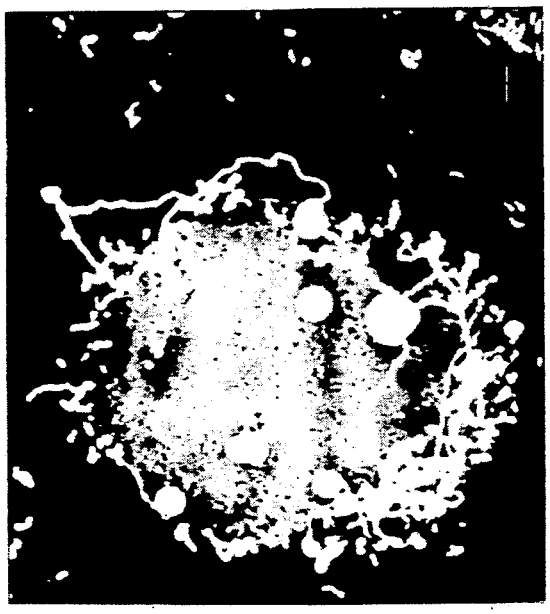
Figure 2C:
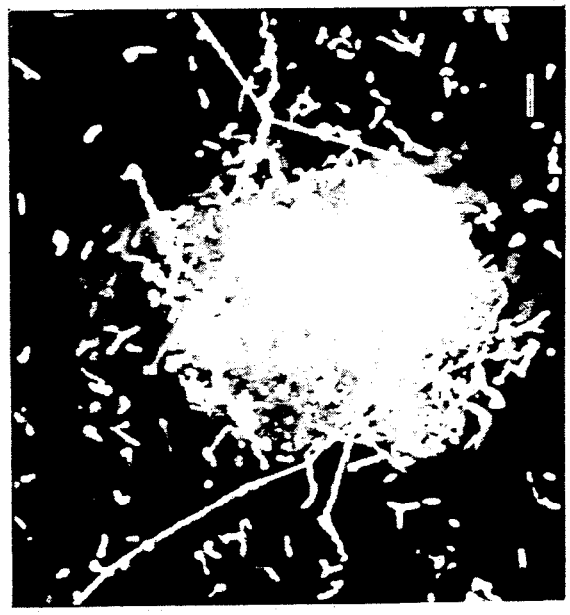

Disintegration of cell membranes by fatty acid. Negative staining of VSV treated with fatty acids suggested that virus inactivation results from disruption of the viral envelope, which is derived from the host cell plasma membrane. To study the effect on cell membranes, monolayers of Vero cells or sheep fibroblasts were incubated at 37° C. for 30 min. in MM with or without 1 mg of linoleic acid per ml and examined by scanning electron microscopy. Control cells incubated in MM without fatty acids showed intact cell membranes (FIG. 2c), whereas in cell layers treated with 1 mg of linoleic acid per ml, the cell membranes were partly or completely disintegrated (FIG. 2d), causing cell lysis. The same effect was seen by incubation of cells with human milk which had been stored at 4° C. for 4 days (FIG. 2b). This milk sample (no. 1)(Table 1) contained 7 mg of fatty acids per ml and was high antiviral. On the other hand, milk sample 1 stored at −86° C. for 4 days (Table 1) showed no effect on cell membranes (FIG. 2a).

Figure 1C:

The micrographs in FIGS. 1a to 1c reflect negative staining of VSV particles showing the effect of linoleic acid treatment. Titration of the samples used for electron microscopy showed a ≦10-fold reduction in virus titer with 0.5 mg of linoleic acid per ml whereas 1 mg/ml caused a ≧10,000-fold reduction. Similar results were obtained by negative staining of VSV incubated with low concentrations of arachidonic acid.

It was next examined whether the effects of antiviral fatty acids were additive so that changes in the concentration of one antiviral component in a mixture can be compensated for by increasing or adding another fatty acid. Mixtures of fatty acids were made in which individual fatty acid concentrations had been found to either not inactivate the virus, or to reduce the titer by less than 10-fold. Mixtures were incubated with virus in maintenance medium. The results are set forth in Table 4. The ability to make antiviral mixtures of medium and long-chain fatty acids indicates that a balance can be made between the potentially toxic effects of high concentrations of medium chain fatty acids in vivo and the loss of antiviral long-chain fatty acids by binding to serum albumin and other blood proteins.

Effect of Antiviral Milk Samples on HIV Titers. Human milk and stomach contents samples that have been found to kill HSV-1 and VSV were tested against HIV (AIDS virus). The results are set forth in Table 5.

As with assays of other enveloped viruses, HIV was diluted five-fold with sIgA depleted milk or stomach contents. Therefore, anti-HIV activity in the undiluted sample is greater than the 1,000-100,000-fold reduction in titer in the assay mix. The results also show that HIV is as sensitive to inactivation by milk lipids as the other enveloped viruses that were tested. It should, therefore, be possible to screen large numbers of lipid mixtures against HSV-1, for example, which is much less expensive to assay than HIV and then test only the promising mixtures against HIV.

Effect of an Antiviral Monoglyceride on CMV Titers. Monocaprin (10:0) which had previously been found to inactivate HSV-1 at a concentration of 2 mM was tested against three separate CMV strains. Incubations were performed in a maintenance medium containing 10% serum. The results, which are set forth in Table 6, establish that CMV as well as HSV-1, HIV and other enveloped viruses can be inactivated in a serum-containing medium.

Monoglyceride Inactivation of HSV-1 in Human Serum. HSV-1 was added directly to human serum, and virus inactivation was measured in the presence of either monocaprin (10:0) or monolaurin (12:0). The results are set forth in Table 7.

Monolaurin at 4 mg/ml reduced serum HSV-1 titer by only 100-fold whereas monocaprin at the same concentration decreased the viral titer by $\geq$ 10,000-fold. In our in vitro studies, monolaurin had more antiviral activity on a concentration basis (millimolar) than monocaprin. The serum results suggest that nonspecific interactions in serum and presumably plasma and other blood products are as important as inherent antiviral activity for determining which monoglycerides to add to human blood and blood products to inactivate viral pathogens.

Monoglyceride Inactivation of HSV-1 in Infant Formula. When monoglycerides were added to another complex fluid, infant formula (Enfamil), differences in HSV-1 killing were found as they were in human serum. As can be seen from the results set forth in Table 8, in infant formula, as in human serum, monocaprin appears to be the most effective monoglyceride against enveloped viruses. In maintenance medium monolinolein produced the same reduction in viral titer as monocaprin but at one-third the concentration (millimolar). In infant formula monocaprin at the concentration used was over 60-fold more effective than monolinolein.

Effect of Added Monoglyceride on RBCs and WBCs in Human Blood. A monocaprin concentration of 3 mg/ml that had previously been shown to be antiviral was added to whole human blood samples and red blood cell and total white blood cell counts were compared to those in the same sample before lipid addition. The results in Table 9 show that a monocaprin concentration that will kill $\geq$ 4.0 log$_{10}$ of enveloped virus when added to human serum does not lyse either RBCs or WBCs in whole blood.

Antibacterial Effect of Human Milk and Purified Monoglycerides. Fatty acids and monoglycerides are antibacterial as well as antiviral. Stomach contents (supplied by Dr. William C. Heird, Columbia Presbyterian Medical Center) from infant fed human milk by gastric intubation were tested for antibacterial activity against Staphylococcus epidermidis (gram +), Escherichia coli (gram −) and Salmonella enteritidis (gram −). See Table 10.

Stomach contents that were antiviral were also antibacterial, killing both gram+ and gram− bacteria Since human milk contains both medium chain and long-chain fatty acids, we next determined whether gram+ and gram− bacteria were equally sensitive to different chain lengths. The results are set forth in Table 11.

Gram positive bacteria were inactivated comparably by medium chain saturated and long-chain unsaturated monoglycerides. However, the gram− bacteria *E. coli* and *S. enteritidis* were unaffected by long-chain unsaturated fatty acids and monolaurin. *H. influenzae* was inactivated by monolaurin so that there are differential sensitivities to MGs between different gram− bacteria. Differences in bacterial inactivation may be due to the bacterial wall, membrane or both. We have taken scanning electron micrographs (not shown) of *S. epidermidis* treated with monolaurin and found that the bacteria were completely disintegrated. It is therefore possible to manipulate MGs and their concentrations to lyse some membranes and leave others intact.

DISCUSSION

Human milk becomes antiviral not only upon storage but also in the stomach of infants within one hour of feeding. The appearance of antiviral activity in stored milk is related to the level of lipoprotein lipase in the milk, indicating that it is caused by the release of fatty acids or other products of lipid hydrolysis. Similar results were previously reported by Welsh et al. (I, II). Data herein indicate that the antiviral effect of stored human milk is caused by lipolysis, and of the nine fatty acids most commonly found in human milk, seven are highly active in killing enveloped viruses. The polyunsaturated long-chain fatty acids were the most active, but medium-chain saturated fatty acids, particularly lauric and myristic acids, also showed activity. Monocaprin and monolaurin were active in concentrations 10 times lower than those of the corresponding free acids, but monomyristin was consistently less active. Long-chain saturated fatty acids, which make up about 30% of the fatty acids in human milk, and short-chain fatty acids, which are more common in cow milk, were not, or were very slightly, antiviral. The concentrations of fatty acids found to reduce viral titers by $\geq$ 10,000-fold in vitro (Table 2) are in the same range of fatty acid concentrations found in human milk. The results indicate that as lipolysis of milk triglycerides proceeds, either during storage or in the gastrointestinal tract, two types of antiviral lipids, monoglycerides and free fatty acids, are produced. It is possible that these two classes of lipid differ in efficacy against intestinal pathogens. This may also be true for the members of each lipid class.

The results are similar to those of earlier studies with different viruses and further establish the marked antiviral effect of most fatty acids found in milk. The electron microscope study suggests that the antiviral effect is caused primarily by disintegration of viral envelopes by fatty acids. Similar findings were reported by Sarkar et al., who treated mouse mammary tumor virus with the cream fraction of human milk and noted degradation of the viral envelope. Our study also shows disintegration of the plasma membrane of cultured cells with concentrations of fatty acids and stored human milk that inactivate viruses. The fatty acids and monoglycerides which have been found to be strongly antiviral were shown to induce fusion of cell membranes. Although the exact mechanism is not clear, it has been suggested that the fatty acids and their monoesters are incorporated into the lipid membrane, causing destabilization of the bilayer. A similar mechanism might lead to the complete disintegration of cell membranes and viral envelopes we observed. We did not compare the sensitivity of cells and enveloped viruses at various fatty acid concentrations. However, a study using hydrophobic alcohols showed that viruses are killed at concentrations that apparently had no effect on cultured cells.

Several studies have indicated a lower incidence of infections, particularly gastrointestinal, in breast-fed versus bottle-fed infants. However, the role of milk fatty acids and their derivatives in protecting babies against illness is not established, despite their well-known antimicrobial effect in vitro. Although most known gastrointestinal viruses are nonenveloped, necrotizing enterocolitis in infants is caused by an enveloped virus, i.e., a human enteric coronavirus. Giardia lamblia, an intestinal protozoan parasite infecting children, is killed by milk fatty acids in vitro, suggesting the possibility of a giardiacidal effect of fatty acids in the intestines. Since fatty acids lyse cells by disrupting their plasma membranes, it is likely that they kill not only giardia but also other parasitic protozoa. Although a few studies have demonstrated antimicrobial activity of human and animal stomach contents after milk feeding, much more work is needed to characterize the active factors and to establish their role in prevention of, and recovery from, gastrointestinal infections.

It is within the scope of the invention that fatty acids and/or monoglycerides thereof are used for antiviral and/or antibacterial activity. The compounds used can be selected from the group consisting of saturated or unsaturated fatty acids having from 4 to 22 carbon atoms and esters of glycerol with said acids. Preferred compounds comprise saturated fatty acids having from 6 to 14 carbon atoms and monoglycerides thereof and mono- or polyunsaturated fatty acids having from 16 to 20 carbon atoms and monoglycerides thereof.

Fatty acids and monoglycerides thereof are readily available. Should it be necessary, desired monoglycerides can be prepared from the corresponding fatty acid or acids by esterification with glycerol according to known procedures.

The above-described compounds have demonstrated antiviral and/or antibacterial activity. It is within the scope of this invention that virus or bacteria-containing media, such as blood, can be treated with an effective amount of one or more fatty acids and/or monoglycerides thereof. It is also within said scope that a human or warm-blooded animal having a viral or bacterial condition may be treated for said condition by administration of a composition according to the invention.

For treatment or prophylaxis purposes one or more of the compounds described herein can be administered to a human or warm-blooded animal perorally, parenterally, intravenously, topically, or rectally as active ingredient in customary pharmaceutical compositions, that is, compositions consisting essentially of an inert pharmaceutical carrier and an effective amount of active ingredient, such as tablets, coated pills, capsules, wafers, powders, solutions, suspensions, emulsions, suppositories, creams, and the like. An effective amount for such application of the compounds according to the present invention would be on the order of from about 0.001 to 4 mg/kg of body weight, preferably from about 0.01 to 3 mg/kg of body weight, 1 to 4 times daily.

If the compounds according to the invention are administered for treatment or prophylaxis reasons to a medium such as blood, especially in test tubes or other conventional laboratory, hospital, or medical containers or hardware, the compounds would be administered in more concentrated dosages. It is envisioned that the compounds would be administered in concentrations of from about 10 $\mu$g/ml to 500 mg/ml of blood, preferably from about 25 $\mu$g/ml to 200 mg/ml of blood, more preferably from about 75 $\mu$g/ml to 100 mg/ml of blood.

TABLE 1

Free fatty acids (FFA) and antiviral activity in milk[a]

| Milk sample | Storage temp/time (°C./days) | FFA (mg/ml) | Reduction of VSV titer ($\log_{10}$) | Lipoprotein lipase (U/ml) |
|---|---|---|---|---|
| 1 | −86/4 | 0.5 | 0 | 336 |
|   | 23/4 | 12.0 | 4.0 |   |
|   | 4/4 | 7.0 | 4.0 |   |
| 3 | −86/4 | 0.5 | 0 | 20 |
|   | 23/4 | 2.0 | 0 |   |
|   | 4/4 | 2.0 | 0 |   |

[a]The same results were obtained for milk tested fresh or after storage at −86° C.

TABLE 2

Viral inactivation by incubation with fatty acids at 37° C. for 30 min

| Fatty acid | | Concn[a] in mg/ml (mM) | Reduction of virus titer ($\log_{10}$) | | |
|---|---|---|---|---|---|
| | | | VSV | HSV-1 | VV[b] |
| Butyric | (4:0)[c] | 10 (113) | 0 | ND[d] | ND |
| Caproic | (6:0) | 10 (86) | 0 | ND | ND |
| Caprylic | (8:0) | 10 (69) | 1.8 | ND | ≧3.2 |
| Capric | (10:0) | 4 (22) | ≧4.0[e] | ≧4.0 | ≧3.2 |
| Lauric | (12:0) | 2 (10) | ≧4.0 | ≧4.0 | ≧3.2 |
| Myristic | (14:0) | 4 (16) | ≧4.0 | ≧4.0 | 1.7 |
| Palmitic | (16:0) | 20 (78) | 1.0 | 1.0 | 0.7 |
| Palmitoleic | (16:1) | 2 (15) | ≧4.0 | ≧4.0 | ≧3.2 |
| Stearic | (18:0) | 20 (70) | 0 | ND | ND |
| Oleic | (18:1 cis) | 2 (7) | ≧4.0 | ≧4.0 | ≧3.2 |
| Elaidic | (18:1 trans) | 2 (7) | ≧4.0 | ND | ND |
| Linoleic | (18:2) | 1 (3.5) | ≧4.0 | ≧4.0 | ≧3.2 |
| Linolenic | (18:3) | 1 (3.6) | ≧4.0 | ≧4.0 | ≧3.2 |
| Arachidonic | (20:4) | 0.5 (1.6) | ≧4.0 | ND | ND |

[a]Concentration of fatty acid in virus mixtures incubated at 37° C. for 30 min. All fatty acids were tested in a series of twofold concentrations. Shown is either the lowest concentration which reduced the VSV titer by ≧4.0 $\log_{10}$ units or the highest concentration tested (butyric, caproic, caprylic, palmitic, and stearic).
[b]VV, Visna virus.
[c]Carbon atoms:double bonds.
[d]ND, Not done.
[e]The titer ($\log_{10}$) of the control virus incubated with mm was 5.5, whereas no virus was detectable in the $10^{-2}$ to $10^{-5}$ dilutions of fatty acid-virus mixtures. It was not possible to test these mixtures in lower dilutions ($10^{-1}$ or undiluted) because they were toxic to the cell cultures. Assuming that the $10^{-1}$ dilution contained infectious virus, the highest possible titer of the fatty acid-virus mixture was $10^{1.5}$ TCID$_{50}$, and the reduction of virus titer ($\log_{10}$) would equal 4.0 (5.5 minus 1.5). If the titers of the mixtures were less than $10^{1.5}$, the reduction of titer would be greater than 4.0.

TABLE 3

Viral inactivation by incubation with monoglycerides at 37° C. for 30 min

| Monoglyceride | | Concn[a] in mg/ml (mM) | Reduction of virus titer ($\log_{10}$) | |
|---|---|---|---|---|
| | | | VSV | HSV-1 |
| Monocaprylin | (8:0)[b] | 2.0 (9) | ≧4.0 | ND[c] |
| Monocaprin | (10:0) | 0.5 (2) | ≧4.0 | ≧3.7 |
| Monolaurin | (12:0) | 0.25 (0.9) | ≧4.0 | ≧3.7 |
| Monomyristin | (14:0) | 2.0 (13) | 3.0 | ND |
| Monoolein | (18:1) | 1.0 (2.8[d]) | 2.3 | ND |
| Monolinolein | (18:2) | 0.25 (0.7) | ≧4.0 | ND |

[a]Lowest concentration causing ≧3.0 $\log_{10}$ reduction in virus titer.
[b]Carbon atoms:double bonds.
[c]ND, Not done.
[d]Highest antiviral activity of the concentrations tested (0.5 to 4 mg/ml). The same results were obtained when the monoglyceride was dissolved in ethanol and diluted 1:100 in mm before being added to the virus.

TABLE 4

Antiviral Activity of Fatty Acid Mixtures

| Fatty Acid Mixture | Individual Fatty Acid Conc. (mg/ml) | Total Fatty Acid Conc. (mg/ml) | Reduction of VSV titer ($\log_{10}$) |
|---|---|---|---|
| Capric | 2 | 3 | ≧3.7 |
| Lauric | 1 | | |
| Lauric | 1 | 2 | ≧3.7 |
| Myristic | 1 | | |
| Lauric | 1 | 2 | ≧3.7 |
| Oleic | 1 | | |
| Oleic | 1 | 1.5 | ≧3.7 |
| Linoleic | 0.5 | | |
| Lauric | 0.7 | | |
| Oleic | 0.7 | 1.7 | ≧3.7 |
| Linoleic | 0.3 | | |

TABLE 5

HIV Inactivation by Antiviral Human Milk

| Sample | Storage | Reduction of HIV titer ($\log_{10}$) |
|---|---|---|
| 1 | Fresh | 0 |

TABLE 5-continued

HIV Inactivation by Antiviral Human Milk

| Sample | Storage | Reduction of HIV titer ($\log_{10}$) |
|---|---|---|
| 1 | 4° | 5.0 |
| 2 | Fresh | 0 |
| 2 | 4° | 5.0 |
| 3 | Fresh | 0 |
| 3 | 4° | 3.5 |
| 4 | Fresh | 0 |
| 4 | Stomach Contents (3 hr) | 3.0 |

TABLE 6

Inactivation of CMV by a Purified Lipid

| CMV Strain Tested | Reduction of CMV Titer ($\log_{10}$ TCID 50%)* |
|---|---|
| AD 169 | ≧3.69 |
| Espilat | ≧3.50 |
| Towne | ≧2.67 |

*TCID 50% = Tissue culture infective dose 50% expressed as $\log_{10}$.

TABLE 7

HSV-1 Inactivation in Human Serum

| Added Monoglyceride* | Reduction in HSV-1 titer ($\log_{10}$) |
|---|---|
| Control | 0 |
| Monocaprin 1 mg/ml | 0.8 |
| Monocaprin 2 mg/ml | 1.8 |
| Monocaprin 4 mg/ml | ≧4.0 |
| Monolaurin 1 mg/ml | 0.8 |
| Monolaurin 2 mg/ml | 1.5 |
| Monolaurin 4 mg/ml | 2.0 |

*The incubation mixture contained human serum, HSV-1 (titer 5.5) and the indicated monoglyceride.

TABLE 8

HSV-1 Killing in Infant Formula

| Added Monoglyceride* | | Reduction in HSV-1 titer ($\log_{10}$) |
|---|---|---|
| Monocaprin | 0.5 mg/ml | 0 |
| | 1 mg/ml | 0.3 |
| | 2 mg/ml | 2.3 |
| Monolaurin | 0.5 mg/ml | 0.3 |
| | 1 mg/ml | 0.3 |
| | 2 mg/ml | 1.0 |
| Monoolein | 0.5 mg/ml | 0 |
| | 1 mg/ml | 0 |
| | 2 mg/ml | 0 |
| Monolinolein | 0.5 mg/ml | 0 |
| | 1 mg/ml | 0.3 |
| | 2 mg/ml | 0.5 |

*The incubation mixture contained formula, HSV-1 (titer 5.5) and the indicated monoglyceride.

TABLE 9

Stability of Blood Cells to Added Monoglyceride

| | Red Blood Cells* | | White Blood Cells* | |
|---|---|---|---|---|
| Sample | Untreated | Treated | Untreated | Treated |
| 1 | 4.59 | 4.46 | 8.8 | 10.2 |
| 2 | 5.10 | 4.78 | 6.9 | 7.7 |
| 3 | 5.30 | 5.19 | 7.7 | 8.5 |
| 4 | 4.94 | 4.74 | 6.3 | 7.4 |
| 5 | 5.08 | 4.36 | 10.3 | 11.1 |

*units - $10^3$/cu mm  *units - $10^6$/cu mm

TABLE 10

Antiviral and Antibacterial Activity of Human Milk Stomach Contents[x]

| | $\log_{10}$ Reduction in HSV-1 Titer by 1 Hour Human | $\log_{10}$ Reduction in Bacterial[xx] Titer by 1 Hour Stomach Contents | | |
|---|---|---|---|---|
| Sample | Stomach Contents | S. epidermidis | E. coli | S. enteritidis |
| 1 | ≧4.0 | | ≧5.0 | |
| 2 | ≧4.0 | ≧5.0 | ≧4.0 | ≧4.0 |
| 3 | ≧4.0 | ≧4.0 | | |
| 4 | ≧4.0 | | | |

[x]The milks themselves were all tested for antiviral and antibacterial activity and none was detected.
[xx]Each sample was not tested against all the bacterial strains because there was not a sufficient volume of stomach contents.

TABLE 11

Inactivation of Gram+ and Gram− Bacteria by Monoglycerides

| | | Reduction of bacterial concentration $\log_{10}$ | | | | |
|---|---|---|---|---|---|---|
| Monoglyceride[1] | | E. coli[2] | S. enteritidis[2] | H. influenze[2,3] | S. epidermidis[4] | Group B[4] streptococcus |
| Monocapryloyl | (8:0) | ≧5.0 | — | ≧8.0 | ≧4.0 | — |
| Monocaprin | (10:0) | ≧5.0 | — | ≧8.0 | ≧4.0 | 4.5 |
| Monolaurin | (12:0) | 0 | 0 | ≧8.0 | ≧4.0 | 4.5 |
| Monoolein | (18:1) | 0 | 0 | — | ≧4.0 | — |
| Monolinolein | (18:2) | — | — | — | — | 4.5 |
| Monoeicosenoin | (20:1) | 0 | 0 | — | ≧4.0 | — |

[1]Each MG was used at 2 mg/ml.
[2]gram−.
[3]Hemophilus influenzae.
[4]gram+.

The preceding specific embodiments are illustrative of the practice of the invention. It is to be understood, however, that other expedients known to those skilled in the art or disclosed herein may be employed without departing from the spirit of the invention or the scope of the appended claims.

We claim:

1. A method of killing enveloped viruses in a host human or warm-blooded animal, which comprises perorally, parenterally, intravenously, or rectally administering to said host an effective antiviral amount of one or more compounds selected from the group consisting of fatty acids having from 6 to 14 carbon atoms and monoglycerides of said fatty acids.

2. The method of claim 1, wherein the fatty acids are saturated fatty acids.

3. The method of claim 1, wherein the enveloped viruses are AIDS viruses.

4. The method of claim 1, wherein the enveloped viruses are herpes viruses.

5. A method of killing enveloped viruses in blood which comprises contacting said blood with an effective antiviral amount of one or more compounds selected from the group consisting of fatty acids having from 6 to 14 carbon atoms and monoglycerides of said fatty acids.

6. The method of claim 5, wherein the fatty acids are saturated fatty acids.

7. The method of claim 5, wherein the enveloped viruses are AIDS viruses.

8. The method of claim 5, wherein the enveloped viruses are herpes viruses.

9. The method of claim 5, wherein the blood is in test tubes.

* * * * *